(12) United States Patent
Miñano Molina et al.

(10) Patent No.: US 12,054,779 B2
(45) Date of Patent: Aug. 6, 2024

(54) CIRCULATING miRNAs AS BIOMARKERS FOR DIAGNOSIS OF MILD COGNITIVE IMPAIRMENT AND ALZHEIMER'S DISEASE

(71) Applicants: UNIVERSITAT AUTONOMA DE BARCELONA, Bellaterra (ES); CENTRO INVESTIGACION BIOMEDICA EN RED ENFERMEDADES NEURODEGENERATIVAS (CIBERNED), Madrid (ES)

(72) Inventors: Alfredo Jesus Miñano Molina, Bellaterra (ES); Dolores Siedlecki Wullich, Bellaterra (ES); Jose Rodriguez Alvarez, Bellaterra (ES)

(73) Assignees: Universitat Autònoma de Barcelona, Bellaterra (ES); Centro Investigacion Biomedica En Red Enfermedades Neurodegenerativas (CIBERNED), Madrid (ES)

( * ) Notice: Subject to any disclaimer, the term of this patent is extended or adjusted under 35 U.S.C. 154(b) by 904 days.

(21) Appl. No.: 17/252,126

(22) PCT Filed: Jun. 13, 2019

(86) PCT No.: PCT/EP2019/065458
§ 371 (c)(1),
(2) Date: Dec. 14, 2020

(87) PCT Pub. No.: WO2019/238807
PCT Pub. Date: Dec. 19, 2019

(65) Prior Publication Data
US 2021/0262030 A1    Aug. 26, 2021

(30) Foreign Application Priority Data

Jun. 15, 2018  (EP) .................................... 18382427

(51) Int. Cl.
*C12Q 1/6883*    (2018.01)

(52) U.S. Cl.
CPC ...... *C12Q 1/6883* (2013.01); *C12Q 2600/112* (2013.01); *C12Q 2600/158* (2013.01); *C12Q 2600/178* (2013.01)

(58) Field of Classification Search
CPC ............ C12Q 1/6883; C12Q 2600/112; C12Q 2600/158; C12Q 2600/178
USPC .... 435/6.1, 91.1, 91.31, 455; 536/23.1, 24.5
See application file for complete search history.

(56) References Cited

FOREIGN PATENT DOCUMENTS

| EP | 3269823 A1 | 1/2018 |
|----|------------|--------|
| EP | 3299473 A1 | 3/2018 |
| WO | 2011057003 A2 | 5/2011 |
| WO | 2012145363 A1 | 10/2012 |
| WO | 2013003350 A2 | 1/2013 |
| WO | 2013022953 A2 | 2/2013 |
| WO | 2015012541 A2 | 1/2015 |
| WO | 2017161256 A1 | 9/2017 |
| WO | 2017186719 A1 | 11/2017 |
| WO | 2019238807 A1 | 12/2019 |

OTHER PUBLICATIONS

International Search Report and Written Opinion for PCT/EP2018/065458 dated Jul. 25, 2019, 15 pages.
Bolstorff, Nachweis und Bedeutung von zirkulierenden microRNAs im Serum von Patienten mit einem Pankreas—oder einem kolorektalen Karzinom, 2018, retrieved from the internet: http://archiv.ub.uni-heidelberg.de/volltextserver/24651/1/Bolstorff,%20Uta%20Lena.pdf.
Affymetrix, GeneChip miRNA 3.0 Array, 2012, retrieved from the internet: http://www.carrerasresearch.org/en/genechip-mirna-3-0-array_38713.pdf.

*Primary Examiner* — Jane J Zara
(74) *Attorney, Agent, or Firm* — Nixon Peabody LLP

(57) ABSTRACT

The invention relates to a specific panel of circulating synaptic protein related miRNAs for use in the diagnosis of Mild Cognitive Impairment (MCI) and/or early diagnosis of Alzheimer's disease (AD). The invention also relates to a method and to a kit for the diagnosis of said diseases using said specific panel of circulating miRNAs biomarkers.

8 Claims, 9 Drawing Sheets
Specification includes a Sequence Listing.

| Patients | First diagnosis | Date | Last diagnosis | Date |
|---|---|---|---|---|
| P1  | MCI | 2006 | AD  | 2017 |
| P2  | MCI | 2007 | AD  | 2011 |
| P3  | MCI | 2006 | AD  | 2017 |
| P4  | MCI | 2006 | NCI | 2007 |
| P5  | MCI | 2005 | AD  | 2008 |
| P6  | MCI | 2007 | NFU | |
| P7  | MCI | 2006 | FTD | 2011 |
| P8  | MCI | 2006 | NCI | 2010 |
| P9  | MCI | 2006 | AD  | 2017 |
| P10 | MCI | 2005 | NFU | |
| P11 | MCI | 2007 | VD  | 2014 |
| P12 | MCI | 2006 | NFU | |
| P13 | MCI | 2007 | AD  | 2017 |
| P14 | MCI | 2006 | MCI | 2017 |
| P15 | MCI | 2006 | AD  | 2013 |
| P16 | MCI | 2006 | NFU | |
| P17 | MCI | 2005 | NFU | |
| P18 | MCI | 2005 | MCI | 2008 |
| P19 | MCI | 2005 | AD  | 2017 |
| P20 | MCI | 2005 | NFU | |
| P21 | MCI | 2005 | AD  | 2006 |
| P22 | MCI | 2006 | NCI | 2007 |
| P23 | MCI | 2005 | NFU | |
| P24 | MCI | 2006 | AD  | 2017 |
| P25 | MCI | 2006 | AD  | 2007 |
| P26 | MCI | 2006 | AD  | 2006 |

FIG. 5

CIRCULATING miRNAs AS BIOMARKERS FOR DIAGNOSIS OF MILD COGNITIVE IMPAIRMENT AND ALZHEIMER'S DISEASE

CROSS-REFERENCE TO RELATED APPLICATIONS

This application is a National Phase of International Application No. PCT/EP2019/065458, filed Jun. 13, 2019, which designated the U.S. and that International Application was published under PCT Article 21(2) in English. This application also includes a claim of priority under 35 U.S.C. § 119(a) and § 365(b) to European patent application No. EP 18382427.5, filed Jun. 15, 2018, the contents of which are herein incorporated by reference in their entirety.

The invention relates to a panel of plasma miRNAs to be used as biomarkers for Mild Cognitive Impairment (MCI) diagnosis and/or early diagnosis of Alzheimer's disease (AD). Therefore, the invention is included in the field of biomedicine and more specifically in the field of diagnosis of MCI and/or AD.

BACKGROUND ART

It is estimated that more that 40 million people worldwide are affected by AD and it is expected that about 100 million could be affected by 2050. Unfortunately there are no treatments to prevent or even reverse AD, making the finding of new therapeutical breakthroughs a huge challenge for our society.

Failure to find effective therapies for AD is related to the limited knowledge about the mechanisms involved and the lack of reliable diagnostic tools during early preclinical stages. Mounting evidence indicates that the effectiveness of therapeutic modalities critically depends on the early diagnosis of AD, before massive neuron loss occurs. Advances in the knowledge of AD have shown that clinical AD symptoms usually develop after a preclinical pathogenic process several decades long, defined as the asymptomatic preclinical stage. This stage is followed by the early clinical AD stage, which occurs in some patients with MCI. Indeed, only a few biomarkers have been described to help differentiate preclinical AD from AD: cerebrospinal fluid levels of total tau, hyperphosphorylated tau and amyloid-β (Aβ)1/42 and accumulation of Aβ in the brain detected by positron emission tomography (Sperling R A et al. Alzheimers Dement. 2011, 7:280-292; Jack C R Jr et al. Lancet Neurol. 2013, 12:207-216; Kadmiri N E et al. Neurosci. 2018, 370:181-190). Unfortunately, all these potential biomarkers could not be used in routine clinical screening due to their invasiveness and economic limitations.

In this sense, a preferable biomarker for clinical applications should be available in biological samples that are easy to obtain in a safe, non-invasive procedure, and the laboratory methods must be reliable, stable, and cost-effective. In light of the preferable biomarker criteria, it becomes clear that progress in AD diagnostics relies to a great extent on the identification of novel diagnostic AD biomarkers of improved sensitivity and specificity, in more easily available diagnostic samples, such as blood.

In recent years, microRNAs (miRNAs, miRs) have emerged as an important novel class of regulatory RNA, which have a profound impact on a wide array of biological processes. One of the most promising approaches to the identification of blood-based AD biomarkers concentrates on circulating miRNAs. Several studies have shown that some miRNAs control the formation, maturation and function of synapses (Schratt G. Nat Rev Neurosci. 2009, 10:842-849) and alteration in their levels could be on the basis of synaptic dysfunction in pathological states (Im H-I and Kenny P. J. Trends Neurosci. 2012, 35: 325-34). Additionally, it has been reported that a number of specific miRNAs are misregulated in AD, including miRNAs implicated in the regulation of key genes involved in AD, such as APP or BACE1, or neuronal function such as glutamate receptors, among others (Millan M J. Prog Neurobiol. 2017; 156:1-68; Hara N et al. Acta Neuropathol. Commun. 2017, 5:10; WO2017186719A1; WO2012145363A1; WO2013024469A1; WO2014075939A1 and WO2013003350A2). Particularly, changes in expression of some miRNAs were found in the brain of Alzheimer's and other neurodegenerative disease patients (Hebert and De Strooper, Trends Neurosci. 32: 199-206, 2009; Saba et al, PLOS One. 2008; 3:e3652).

Despite many biomarkers for AD diagnosis has been disclosed in recent years, there is not a reliable and clinically useful panel of biomarkers for early AD diagnosis, because of difficulties with the standardization of the analytical methods and the low reproducibility of the disclosed results. Indeed, earlier definitive diagnosis of AD, ideally prior to clinical manifestations of the disease, would facilitate earlier and potentially more effective treatment of patients affected with AD.

In this sense, there is an urgent need to identify, definitive reliable and clinically useful biomarkers for AD diagnosis, preferably at early stages, prior to clinical manifestations, with high sensitive and specific capacity.

SUMMARY OF THE INVENTION

Deficits in synaptic function are likely to be involved in the development of AD in its preclinical stages, such as MCI. The inventors have identified that a panel of specific miRNAs related to synaptic proteins are upregulated in biological isolated samples from preclinical AD (MCI) and AD subjects, but no changes are observed in plasma from frontotemporal dementia (FTD) patients. Thus, the invention show that the expression levels of synaptic protein related miRNAs selected from the group miR-92a, miR-181c and miR-210 are upregulated, in an isolated biological sample, preferably in plasma, from subjects suffering MCI, a preclinical AD and from AD subjects, versus healthy subjects.

Moreover, the data showed in the present disclosure demonstrate that the combined analysis of the three miRNAs presented high diagnosis accuracy for distinguishing both MCI and AD subjects from healthy controls and it could be used as a reliable early diagnostic tool for distinguishing MCI and/or AD from healthy subjects. Tables 2 and 3 show that the panel of miRNAs biomarkers of the present invention: miR-92a, miR-181c and miR-210 clearly distinguish with a high sensitivity and specificity the preclinical stages of AD (MCI) as well as AD patients from healthy controls.

The panel of the miRNAs biomarkers of the present invention is cost-effective, significantly simpler for handling, much easier to use and more immediately implementable in clinical settings, than any of the existing biochemical or brain imaging assays.

Thus, in a first aspect, the invention relates to a panel or signature of miRNAs related to synaptic proteins, hereinafter the panel or signature of miRNAs of the invention, comprising the miR-92a, miR-181c and miR-210 for use as biomarker for the diagnosis of MCI and/or early stages of AD development, preferably for the diagnosis of MCI and/or AD. In a preferred embodiment, the panel or signature of miRNAs of the invention consisting of the miR-92a, miR-181c and miR-210. In a more preferred embodiment, the miR-92a is the miR-92a-3p (SEQ ID NO: 1), the miR-181c is the miR-181c-5p (SEQ ID NO: 2) and the miR-210 is the miR-210-3p (SEQ ID NO: 3).

In a second aspect the invention refers to the in vitro use of the panel of miRNAs of the invention, hereinafter the use of the panel or signature of miRNAs of the invention, as biomarker for MCI and/or early stages of AD. In a more preferred embodiment the miR-92a is the miR-92a-3p (SEQ ID NO: 1), the miR-181c is the miR-181c-5p (SEQ ID NO: 2) and the miR-210 is the miR-210-3p (SEQ ID NO: 3).

In another aspect, the present invention refers to an in vitro method, hereinafter the in vitro method of the invention, for the diagnosis of MCI and/or early stages of AD in an isolated biological sample of a subject, wherein the method comprises:

a) quantifying the expression levels of the panel of miRNAs of the invention in the isolated biological sample of the subject,
b) comparing the value obtained in step (a) to a standard value, and
c) assigning the subject to the group of patients suffering from MCI and/or AD when the value obtained in step (a) is significantly higher than the standard value.

In another aspect, the present invention refers to a kit or device, hereinafter the kit or device of the invention, for the in vitro diagnosis of MCI and/or early stages of AD, comprising primers or probes specific for the panel of miRNAs of the present invention.

In another further aspect, the present invention refers to the use of the kit or device of the present invention, hereinafter the use of the kit or device of the invention, for the in vitro diagnosis of MCI and/or early stages of AD.

DESCRIPTION OF THE DRAWINGS

FIG. 5. Follow-up of MCI patients. P: patient. MCI: Mild cognitive impairment. AD: Alzheimer's Disease. FTD: Frontotemporal dementia. VD: Vascular dementia. NCI: No cognitive impairment. NFU: No follow-up available.

DETAILED DESCRIPTION OF THE INVENTION

Figure 1A:
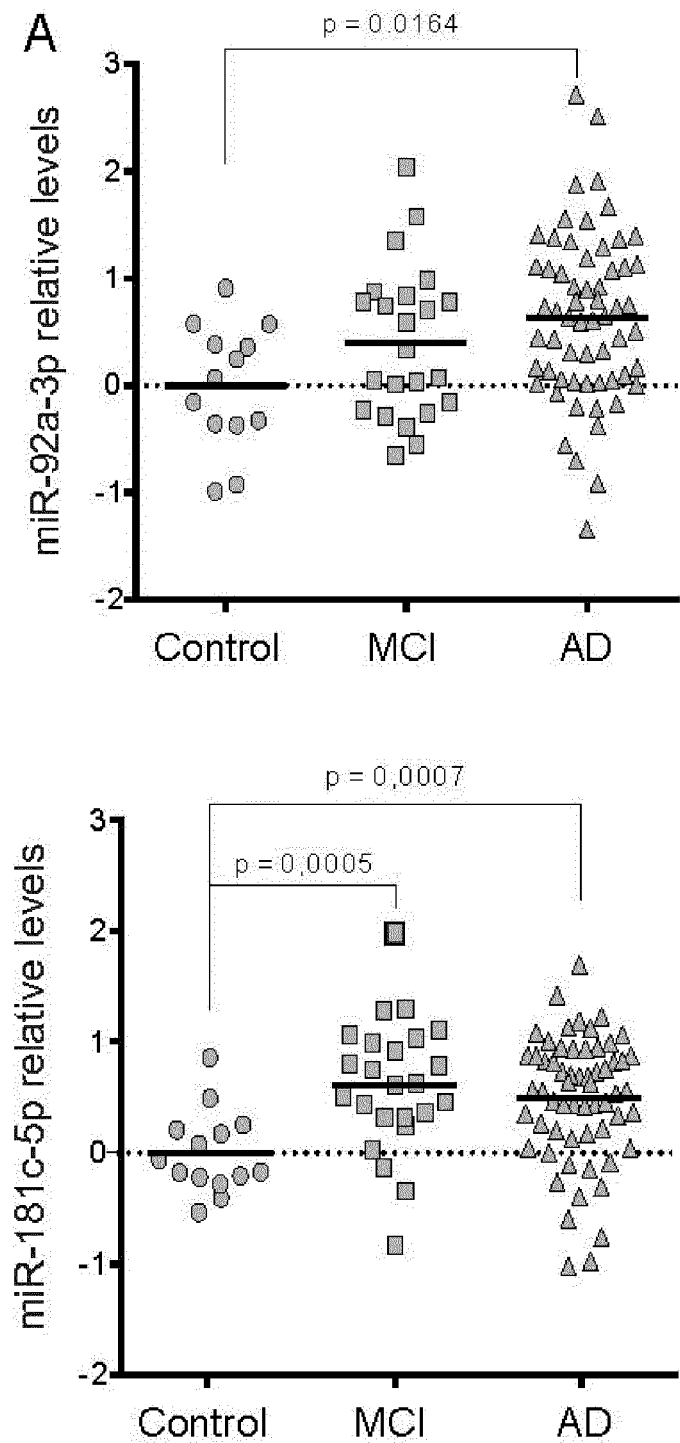
FIG. 1. Circulating miRNA levels at different stages of AD pathology compared with cognitively normal controls (A). Log2 transformed data were normalized versus the geometric mean of miR-191-5p and miR-484 levels. (B) Receiver operating characteristic (ROC) curve analysis was performed to distinguish MCI (dotted) and AD (continuous) cases from healthy controls. Area under the curve (AUC) is shown for each miRNA and stage.
Figure 1A:
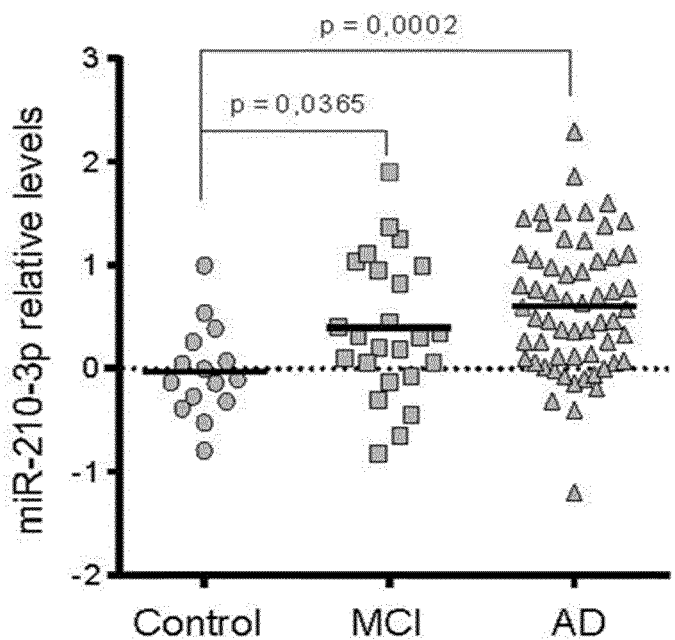

The authors of the present invention have found that the analysis of the expression levels of the panel of miRNAs of the invention, related to synaptic proteins, are upregulated in biological isolated samples from MCI and AD subjects versus healthy controls. The data of the present invention show that the panel of miRNAs biomarkers comprising the miRNAs selected from the list consisting of: miR-92a, miR-181c and miR-210, preferably the miR-92a-3p (SEQ ID NO: 1), the miR-181c-5p (SEQ ID NO: 2) and the miR-210-3p (SEQ ID NO: 3), clearly distinguish, with a high sensitivity and specificity, MCI and/or early stages of AD, such as AD patients from healthy controls. This finding opens the door to new molecular signature as biomarker in the diagnosis of MCI and/or early stages of AD.

Based on these findings, the inventors have developed the products, methods and uses of the present invention which will be described now in detail.

In a first aspect, the present invention refers to a panel of miRNAs related to synaptic proteins comprising the miRNAs selected from the list consisting of: miR-92a, miR-181c and miR-210 for use as biomarker for diagnosis of MCI and/or early stages of AD.

In a preferred embodiment, the panel of miRNAs consisting of the miRNAs: miR-92a, miR-181c and miR-210.

The term "diagnosis" is considered to be the procedure through which the presence or absence of a disease is identified in a subject, preferably of a neurodegenerative disease, more preferably MCI and/or early stages of AD.

The term "early", as used in this invention, refers to the diagnosis of a disease, preferably of a neurodegenerative disease, more preferably AD, and most preferably a preclinical stage of AD in a subject in the first stages of the disease, that is, before the appearance of clinical symptoms.

A "miRNA" is a short, naturally occurring RNA molecule and shall have the ordinary meaning understood by a person skilled in the art. In a preferably embodiment the panel of miRNAs of the present invention are the miR-92a, miR-181c and miR-210, more preferably, the miR-92a is the miR-92a-3p (SEQ ID NO: 1), the miR-181c is the miR-181c-5p (SEQ ID NO: 2) and the miR-210 is the miR-210-3p (SEQ ID NO: 3).

The term "marker" or "biomarker" refers to a biological molecule, e.g., a nucleic acid, peptide, protein, hormone, etc., whose presence or concentration can be detected and correlated with a known condition, such as a disease state, or with a clinical outcome, such as response to a treatment.

The term "Alzheimer's disease" or "AD", as used in this invention refers to a neurodegenerative disease that is manifested as a cognitive deterioration and behavioural disorder. In its typical form it is characterised by a progressive loss of memory and of other mental capacities, as the neuronal cells degenerate and/or die and different areas of the brain atrophy.

The term "Mild Cognitive Impairment" or "MCI" as used in the present invention refers to a cognitive decline that is greater than expected due to normal aging, and that has been associated with a higher risk of developing AD.

In a more preferred embodiment, the panel of miRNAs of the invention is detected in an isolated biological sample of a subject. In a more preferred embodiment, the expression levels of the panel of miRNAs of the invention are detected and quantified.

The term "subject", as used herein, refers to all animals classified as mammals and includes, but is not restricted to, domestic and farm animals, primates and humans, e.g., human beings, non-human primates, cows, horses, pigs, sheep, goats, dogs, cats or rodents. Preferably, the subject is a human being, more preferably a male or female human of any race.

The term "isolated biological sample" as used in this description refers to a sample, isolated from an organism that might come from a physiological fluid and/or any cell or tissue of the organism. In a more preferred embodiment, the biological sample is a biofluid sample, such as blood, serum, plasma and the like. In a particular embodiment, said sample is a plasma sample. Said samples can be obtained by conventional methods well known to those of ordinary skill in the related medical arts.

The term "expression level" refers, e.g., to a determined level of expression of a nucleic acid of interest, preferably a miRNA. As used in this invention, the term refers to the amount or concentration of the panel of miRNAs biomarkers of the invention used as an indicator of a MCI and/or AD.

The term "quantify" as used in this invention refers to the measurement of the amount or the concentration of the panel of miRNAs of the invention. Measurement refers to the measurement of the amount or concentration of the panel of miRNAs of the invention through techniques for measuring nucleic acids, preferably miRNAs such as, for example but without limitation, RT-PCR, quantitative real time PCR (RT-qPCR), droplet digital PCR (ddPCR) or Southern Blot. More preferably, the measurement of miRNAs of the invention is carried out by RT-qPCR.

All the particular embodiments disclosed previously for the first aspect of the invention are also applicable to the rest of the aspects of the inventions mentioned herein. Likewise, the definitions and techniques provided for the first aspect of the invention are also applicable to the rest of the aspects of the invention.

In another aspect, the present invention refers to the in vitro use of the panel of miRNAs of the invention as biomarker for diagnosis of MCI and/or early stages of AD. In a preferred embodiment, the panel of miRNAs of the invention comprising the miR-92a, the miR-181c and the miR-210. In a more preferred embodiment, the panel of miRNAs of the invention consisting of the miR-92a, the miR-181c and the miR-210. In a more preferred embodiment, the miR-92a is the miR-92a-3p (SEQ ID NO: 1), the miR-181c is the miR-181c-5p (SEQ ID NO: 2) and the miR-210 is the miR-210-3p (SEQ ID NO: 3).

Another aspect of the present invention refers to an in vitro method of diagnosis of MCI and/or early stages of AD, in an isolated biological sample of a subject, wherein the method comprises:
  a) quantifying the expression level of the panel of miRNAs of the invention in the isolated biological sample of the subject,
  b) comparing the value obtained in step (a) to a standard value, and
  c) assigning the subject to the group of patients suffering from MCI and/or AD when the value obtained in step (a) is significantly higher than the standard value.

In a more preferred embodiment of the in vitro method of the invention, the panel of miRNAs comprising the miRNAs selected from the list: miR-92a, miR-181c and miR-210. In a more preferred embodiment, the panel of miRNAs consisting of miR-92a, miR-181c and miR-210.

In a more preferred embodiment the miR-92a is the miR-92a-3p (SEQ ID NO: 1), the miR-181c is the miR-181c-5p (SEQ ID NO: 2) and the miR-210 is the miR-210-3p (SEQ ID NO: 3).

The term "standard value" is considered to mean any value or range of values derived from the quantification of the panel of miRNAs of the invention in a control biological sample from a healthy subject or in a mixture of biological samples derived from a control group. The standard value serving as a reference standard for comparison, such that the test sample may be compared to the standard value, in order to infer the MCI and/or AD in the subject. The standard value or reference level can be an absolute value, a relative value, a value that has an upper or a lower limit, a range of values, an average value, a median value, a mean value, or a value as compared to a particular control or baseline value. As it is mentioned earlier, the standard value according to the present invention can be obtained from one or more subjects who do not suffer from MCI and/or AD (i.e., healthy control subjects). A subject is considered to not suffer from MCI and/or AD if they have not been diagnosed with MCI or AD.

According to the diagnostic method of the invention, the levels or the expression levels of the panel of the miRNAs of the invention is considered "decreased" when the level/expression level of said markers in a sample is lower than its reference value. The level/expression level of a marker is considered to be lower than its reference value when it is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 120%, at least 130%, at least 140%, at least 150%, or more lower than its reference value. Likewise, in the context of the diagnostic method of the invention, the level or the expression level of the panel of the miRNAs of the invention is considered "increased" when the level/expression level of said markers in a sample is higher than its reference value. The level/expression level of a biomarker is considered to be higher than its reference value when it is at least 1.5%, at least 2%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 120%, at least 130%, at least 140%, at least 150%, or more higher than its reference value.

The term "control group" in this description is understood to be a group of healthy subjects, of the same or similar age as the subject under study, from which values or ranges of values of concentration or amount of miRNAs of the invention have been obtained from the quantification of miRNAs in a collection of biological samples from these healthy subjects, and that are representative of the population in which the method of the invention is to be applied. The quantification of the panel of miRNAs of the invention must be made in the same way and be obtained from the same type of isolated biological sample as that from the subject to be studied in step (a) of the method of the invention.

The terms "healthy" or "healthy subject" in this invention are considered to mean a subject or individual not suffering from a neurodegenerative disease, preferably MCI and/or AD.

The term "comparison" or "comparing" as used in this invention refers, but is not limited to, the comparison of the amount of the panel of miRNAs of the invention determined in the biological sample of step (a) with a standard value. The comparison described in step (b) of the method of the invention can be performed manually or assisted by a computer.

Thus, increased levels of the panel of miRNAs of the invention in the sample from said patient is indicative that the patient suffering from MCI and/or AD. According to the present invention, the expression levels of the panel of miRNAs of the invention are estimated to be high with respect to a standard value when the levels in the patient sample show an increase of at least 1.5%, at least 2%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 120%, at least 130%, at least 140%, at least 150% or more.

A "significantly higher" amount than a standard value can be established by an expert in the field through the use of various statistical tools such as, for example but without limitation, by determination of confidence intervals, determination of the p value, two-tailed Student's test, two-sided nonparametric Mann-Whitney test, Fisher's discriminant functions, using Kruskal-Wallis analysis with Dunn's post hoc multiple comparisons test, one-way ANOVA with Bonferroni's post hoc multiple comparisons test or Kruskal-Wallis U tests.

The present invention also contemplates the preparation of kits or devices for use in accordance with the present invention. Suitable kits include various reagents, preferably primers or probes specific for the detection and/or quantification of the panel of miRNAs of the invention, for use in accordance with the present invention in suitable containers and packaging materials, including tubes, vials, and shrink-wrapped and blow-molded packages.

A "probe" is a molecule or substance capable of specifically binding or interacting with a specific biological molecule. The term "primer", "primer pair" or "probe", shall have ordinary meaning of these terms which is known to the person skilled in the art of molecular biology. In a preferred embodiment of the invention "primer", "primer pair" and "probes" refer to oligonucleotide or polynucleotide molecules with a sequence identical to, complementary to, homologues of, or homologous to regions of the target molecule or target sequence which is to be detected or quantified, such that the primer, primer pair or probe can specifically bind to the target molecule, e.g. target nucleic acid, RNA, miRNA, DNA, cDNA, gene, transcript, peptide, polypeptide, or protein to be detected or quantified. As understood herein, a primer may in itself function as a probe. A "probe" as understood herein may also comprise e.g. a combination of primer pair and internal labeled probe, as is common in many commercially available qPCR methods.

The kit or device of the invention may contain positive and negative controls. Preferably, this kit or device also comprises instructions to carry out the quantification of the panel of mirRNAs of the invention according to the description in this invention.

Unless otherwise defined, all technical and scientific terms used herein have the same meaning as commonly understood by one of ordinary skill in the art to which this invention belongs. Methods and materials similar or equivalent to those described herein can be used in the practice of the present invention. Throughout the description and claims the word "comprise" and its variations are not intended to exclude other technical features, additives, components, or steps. Additional objects, advantages and features of the invention will become apparent to those skilled in the art upon examination of the description or may be learned by practice of the invention. The following examples, drawings and sequence listing are provided by way of illustration and are not intended to be limiting of the present invention.

EXAMPLES

The following examples are offered to illustrate, but not to limit, the claimed invention. It is understood that the examples and embodiments described herein are for illustrative purposes only, and persons skilled in the art will recognize various reagents or parameters that can be altered without departing from the spirit of the invention or the scope of the appended claims.

Material and Methods

Subjects

Plasma samples analyzed in this study were obtained from two different cohorts. The first cohort provided by Fundació ACE (Barcelona, Spain) includes 14 healthy controls (HC), 24 MCI and 59 AD patients. The second one was recruited at the Memory Unit of the Hospital Sant Pau (Barcelona, Spain) and consists of 24 HC and 27 FTD patients. Participants were clinically diagnosed by neurologists and classified according to internationally accepted diagnostic criteria. Demographic and clinical characteristics of cohorts 1 and 2 are summarised in Table 1. FTD participants include 19 patients with possible or probable behavioral variant and 6 with semantic variant of primary progressive aphasia. 2 patients with FTD were additionally diagnosed with concomitant amyotrophic lateral sclerosis (ALS) according to El Escorial criteria (Brooks B R et al. Amyotrophic Lateral Sclerosis and Other Motor Neuron Disorders. 2009, 1:5, 293-299).

TABLE 1

Demographic and Clinical characteristics of subjects included in the study.

| | Cohort 1 | | | Cohort 2 | |
|---|---|---|---|---|---|
| | HC | MCI | AD | HC | FTD |
| Cohort size | 14 | 24 | 59 | 24 | 27 |
| Male/Female | 7/7 | 9/15 | 17/43 | 11/13 | 17/10 |
| Age (years) | 68.29 ± 8.9 | 71.38 ± 8.7 | 77.69 ± 6.5 | 67.03 ± 5.05 | 68.87 ± 7.48 |
| GDS | 2.07 ± 0.2 | 3.04 ± 0.2 | 4.60 ± 1.0 | 1 ± 0 | 3.76 ± 0.99 |
| MMSE | 29.21 ± 1.1 | 27.21 ± 2.1 | 16.51 ± 7.3 | 28.5 ± 1.7 | 25.5 ± 3.76 |

HC: Cognitively healthy controls.
MCI: Mild cognitive impairment.
AD: Alzheimer's Disease.
FTD: Frontotemporal dementia.
MMSE: Mini Mental State Examination
GDS: Global Deterioration Scale.
All data are shown as mean ± SD.

Sample Processing, RNA Extraction and Reverse Transcription

Blood samples were collected in EDTA-containing tubes, as recommended by Moldovan, L et al. (Moldovan, L et al. J Cell Mol Med. 2014, 18:371-390). After a 20 minutes centrifugation (2500×g), plasma was separated, aliquoted and stored at −80° C. until use. Plasma samples were thawed in ice for RNA extraction and hemolysis of each sample was analyzed at the time measuring absorbance at 414/375 nm (414/375 ratio >1.4 were considered hemolysed). RNA was isolated from 200 µl of plasma, using the miRNeasy RNA isolation kit (Qiagen) following the manufacturer's indications. 2 µl of RNA was reverse-transcribed to cDNA using TaqMan™ Advanced miRNA cDNA Synthesis Kit (Thermo Fisher Scientific).

miRNAs Quantification by RT-qPCR

Real-time PCR was performed from 5 µl of 1/10 diluted cDNA using TaqMan Fast Advanced Master Mix and specific hydrolysis probes for each miRNA detection (TaqMan Advanced miRNA Assays, Thermo Fisher Scientific, see Table 2). Amplification was performed using the Applied Biosystems 7500 Fast instrument. Samples were run in duplicate and internal control samples were repeated in every plate to avoid batch effects. Raw Ct data acquired using the 7500 Software v2.0.6 (Applied Biosystems) was exported to LinRegPCR software to calculate the amplification efficiency for each reaction. Reactions with amplification efficiency below 1.6 were discarded. Ct values and average efficiencies obtained from LinRegPCR were used to analyze miRNA levels by the comparative ΔΔCt method. To date, there is no consensus on the use of particular reference genes for miRNA levels normalization in AD studies. Therefore, in the present study, the stability of some described reference genes was evaluated using the NormFinder algorithm. hsa-miR-191-5p and hsa-miR-484 were identified as the most stable reference genes along all plasma samples. In addition, hsa-miR-191-5p and hsa-miR-484 showed higher correlation than other candidates (Spearman's correlation coefficient r=0.89; p<0,0001). miRNA levels were normalized versus the geometric mean of selected reference genes, to compensate abundance differences between miRNAs and prevent statistical outliers (Vandesompele, J et al. Genome Biol. 2002, 3: 34-1).

Statistical Analysis

Ct values were normalized versus the Ct mean of control group and log 2 transformed. D'Agostino & Pearson and Shapiro-Wilk tests were used to evaluate data normality. miRNA levels between healthy controls and patients were compared using a two-sided nonparametric Mann-Whitney test. P values of <0.05 were considered statistically significant. Receiver operating characteristic (ROC) curve analysis under a nonparametric approach was used to obtain the area under the curve (AUC) to evaluate sensitivity and specificity of each miRNA as a predictive biomarker. Logistic regression was applied to evaluate biomarker combination by ROC curve analysis. Statistical analysis was performed using GraphPad Prism software v6.01 (GraphPad Software Inc., California, USA) and MedCalc (v17.9.7).

Example 1. Up-Regulation of the Panel of Biomarkers of the Invention: miR-92a, miR-181c and miR-210 in Plasma of MCI and AD Patients The expression levels of the synaptic proteins-related miRNAs of the present invention, miR-92a-3p (SEQ ID NO: 1), miR-181c-5p (SEQ ID NO: 2) and miR-210-3p (SEQ ID NO: 3) (Table 2) were analysed by RT-qPCR in the plasma of a cohort consisting of 14 healthy controls (HC), 24 MCI/probable early AD and 59 sporadic AD subjects (Table 1). Additionally, the expression levels of the miR-584-5p (SEQ ID NO: 4), was also analyses by RT-qPCR in the plasma of the subject mentioned above.

TABLE 2 miRNAs mentioned in the present disclosure.

| miRNA | SEQ ID NO: | Sequence | mirBase Accession |
|---|---|---|---|
| hsa-miR-92a-3p | 1 | UAUUGCACUUGUCCCGGCCUGU | MIMAT0000092 |
| hsa-miR-92a-5p | 7 | AGGUUGGGAUCGGUUGCAAUGCU | MIMAT0004507 |
| hsa-miR-181c-5p | 2 | AACAUUCAACCUGUCGGUGAGU | MIMAT0000258 |
| hsa-miR-181c-3p | 8 | AACCAUCGACCGUUGAGUGGAC | MIMAT0004559 |
| hsa-miR-210-3p | 3 | CUGUGCGUGUGACAGCGGCUGA | MIMAT0000267 |

TABLE 2-continued miRNAs mentioned in the present disclosure.

| miRNA | SEQ ID NO: | Sequence | mirBase Accession |
|---|---|---|---|
| hsa-miR-210-5p | 9 | AGCCCCUGCCCACCGCACACUG | MIMAT0026475 |
| hsa-miR-584-5p | 4 | UUAUGGUUUGCCUGGGACUGAG | MIMAT0003249 |
| hsa-miR-484 | 5 | UCAGGCUCAGUCCCCUCCCGAU | MI0002468 |
| hsa-miR-191-5p | 6 | CAACGGAAUCCCAAAAGCAGCUG | MI0000465 |
| hsa-miR-191-3p | 10 | GCUGCGCUUGGAUUUCGUCCCC | MI0000465 |

ROC curve analysis and AUC determination are considered an objective method for evaluating binary classifiers. ROC curves illustrate a classifier's performance over the range of thresholds for sensitivity and specificity. Sensitivity is the portion of correctly classified positive observations and the specificity is the portion of correctly classified negative observations. The AUC is the summary measure of accuracy which incorporate sensitivity and specificity into a single measure and quantifies the ranking ability of a ranking value (i.e. here expression level of single miRNA). It ranges from 0 to 1. A higher AUC means better classification. A perfect classifier will have ROC curve passing through (1:1) and AUC of 1 (upper left corner of the plot). Random guesser is expected to be diagonal and AUC of 0.5. Balanced accuracy point (Youden Index J) (optimal operating threshold) on ROC curve is the point on the curve for which the sum of sensitivity and specificity is maximal.

In this sense, the data show a significant increase in the plasma levels of miR-92a-3p (SEQ ID NO: 1), miR-181c-5p (SEQ ID NO: 2) and miR-210-3p (SEQ ID NO: 3) in AD patients when compared with HC (FIG. 1A; miR-92a-3p: p=0.0164, log 2 fold change=0.52; miR-181c-5p: p=0.0007, log 2 fold change=0.68; miR-210-3p: p=0.0002, log 2 fold change=0.71). Significant increases were also observed in MCI plasma samples of miR-181c-5p (p=0.0005, log 2 fold change=0.74) and miR-210-3p (p=0.0365, log 2 fold change=0.43) whereas an increasing trend was observed for miR-92a-3p (p=0.1498, log 2 fold change=0.48). By contrast no changes were observed in miR-584-5p expression levels between controls and MCI or AD subjects (data not shown).

Figure 1B:
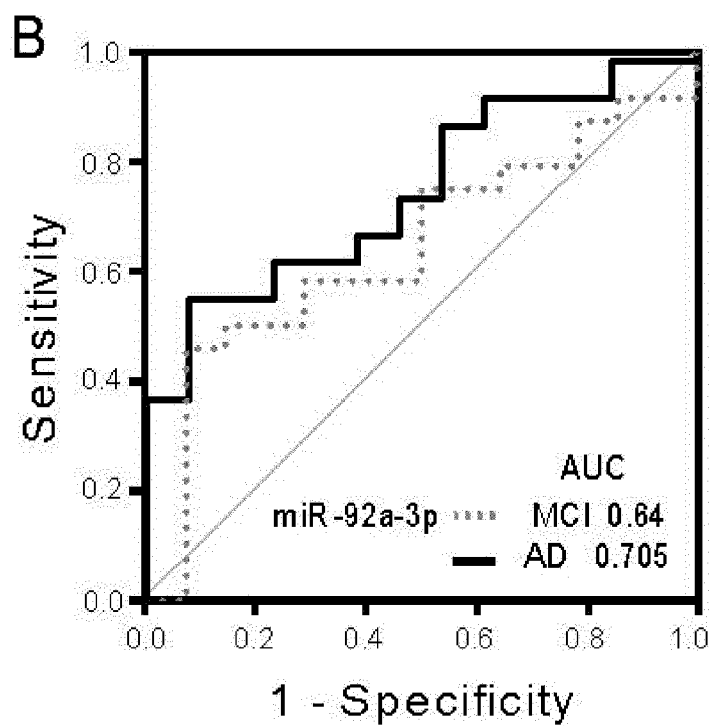
Figure 1B:
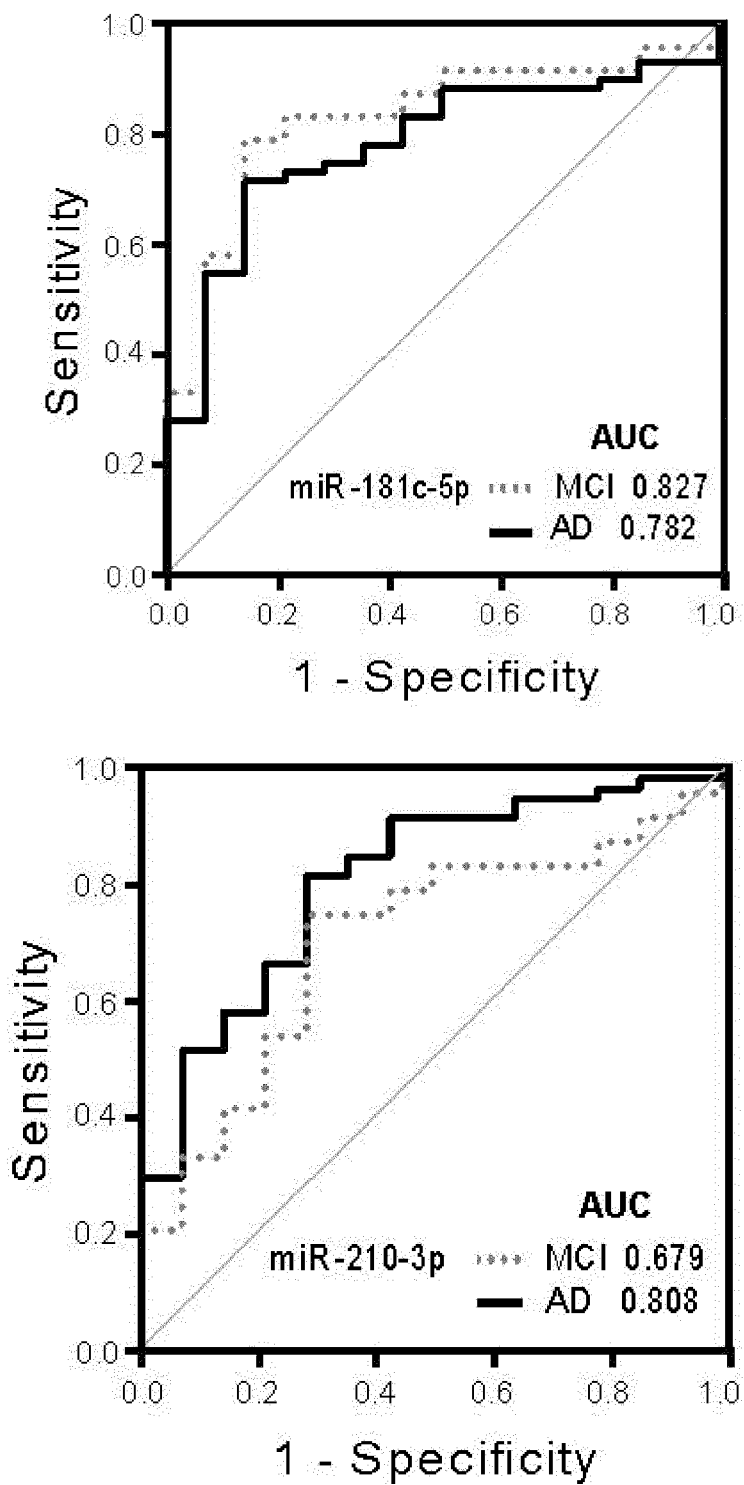

Furthermore, ROC curve analysis was performed to evaluate the diagnostic potential of the panel of the biomarkers of the present invention, miR-92a-3p (SEQ ID NO: 1), miR-181c-5p (SEQ ID NO: 2) and miR-210-3p (SEQ ID NO: 3) (FIG. 1B). The values obtained when compared with MCI subjects for miR-92a-3p, miR-181c-5p and miR-210-3p were: AUC values of 0.64, 0.83 and 0.68 respectively; 45.83%, 79.17% and 70.83% of sensitivity respectively; 92.86%, 85.71%, 71.43% of specificity respectively (Table 3).

TABLE 3

Individual and signature miRNAs performance characteristics in predicting MCI stage. Signature miRNAs performance characteristics in females and males.

| miRNAs (hsa-miR) | AUC | Sensitivity | Specificity | Youden Index J | p-value |
|---|---|---|---|---|---|
| miR-92-3p | 0.643 | 45.83% | 92.86% | 0.4287 | 0.1293 |

TABLE 3-continued

Individual and signature miRNAs performance characteristics in predicting MCI stage. Signature miRNAs performance characteristics in females and males.

| miRNAs (hsa-miR) | AUC | Sensitivity | Specificity | Youden Index J | p-value |
|---|---|---|---|---|---|
| miR-181c-5p | 0.827 | 79.17% | 85.71% | 0.6488 | <0.0001 |
| miR-210-3p | 0.679 | 70.83% | 71.43% | 0.4226 | 0.0452 |
| miR-92-3p/miR-210-5p | 0.667 | 62.50% | 71.43% | 0.3393 | 0.0659 |
| miR-92-3p/miR-181c-5p | 0.821 | 79.17% | 78.57% | 0.5774 | <0.0001 |
| miR-181c-5p/miR-210-5p | 0.836 | 87.50% | 78.57% | 0.6607 | <0.0001 |
| miR-92-3p/miR-181c-5p/miR-210-3p | 0.878 | 87.50% | 85.71% | 0.7321 | <0.0001 |
| Female | 0.810 | 86.67% | 71.43% | 0.5810 | 0.0015 |
| Male | 0.937 | 100.00% | 85.71% | 0.8571 | <0.0001 |

AUC values for miR-92a-3p, miR-181c-5p and miR-210-3p when AD were compared to healthy control subjects were: 0.71, 0.78 and 0.81 respectively (FIG. 1B). Whereas miR-92a-3p has 48.33 of sensitivity and 92.86% of specificity, miR-181c-5p has 71.67% of sensitivity and 85.71% of specificity and miR210-3p has 81.67% of sensitivity and 71.43% of specificity (Table 4).

TABLE 4

Individual and signature miRNAs performance characteristics in predicting AD. Signature miRNAs performance characteristics in females and males.

| miRNAs (hsa-miR) | AUC | Sensitivity | Specificity | Youden Index J | p-value |
|---|---|---|---|---|---|
| miR-92-3p | 0.705 | 48.33% | 92.86% | 0.4119 | 0.0086 |
| miR-181c-5p | 0.782 | 71.67% | 85.71% | 0.5738 | <0.0001 |
| miR-210-3p | 0.808 | 81.67% | 71.43% | 0.5310 | 0.0001 |
| miR-92-3p/miR-210-5p | 0.814 | 88.33% | 64.29% | 0.5262 | 0.0001 |
| miR-92-3p/miR-181c-5p | 0.795 | 85.00% | 71.43% | 0.5643 | <0.0001 |
| miR-181c-5p/miR-210-5p | 0.861 | 85.00% | 78.57% | 0.6357 | <0.0001 |
| miR-92-3p/miR-181c-5p/miR-210-3p | 0.864 | 93.33% | 71.43% | 0.6476 | <0.0001 |
| Female | 0.820 | 90.48% | 71.43% | 0.6190 | 0.0006 |
| Male | 0.921 | 74.07% | 100.00% | 0.7404 | <0.0001 |

Combinated ROC analysis of miR-92a-3p, miR-181c-5p and miR-210-3p provides a higher diagnostic value for MCI and AD, showing that this panel of miRNAs could be used as a molecular signature for early diagnosis of MCI and/or AD. In this sense the data obtained by the analysis of the panel of biomarkers of the present invention show that an AUC value of 0.88, a 87.5% of sensitivity and a 85.71% of specificity to distinguish MCI from controls (FIG. 2B and Table 3) was achieved. This molecular miRNA signature provides an AUC value of 0.86, a 93.33% of sensitivity and a 71.43% of specificity when AD patients were compared to controls (FIG. 2B and Table 3).

Figure 2:
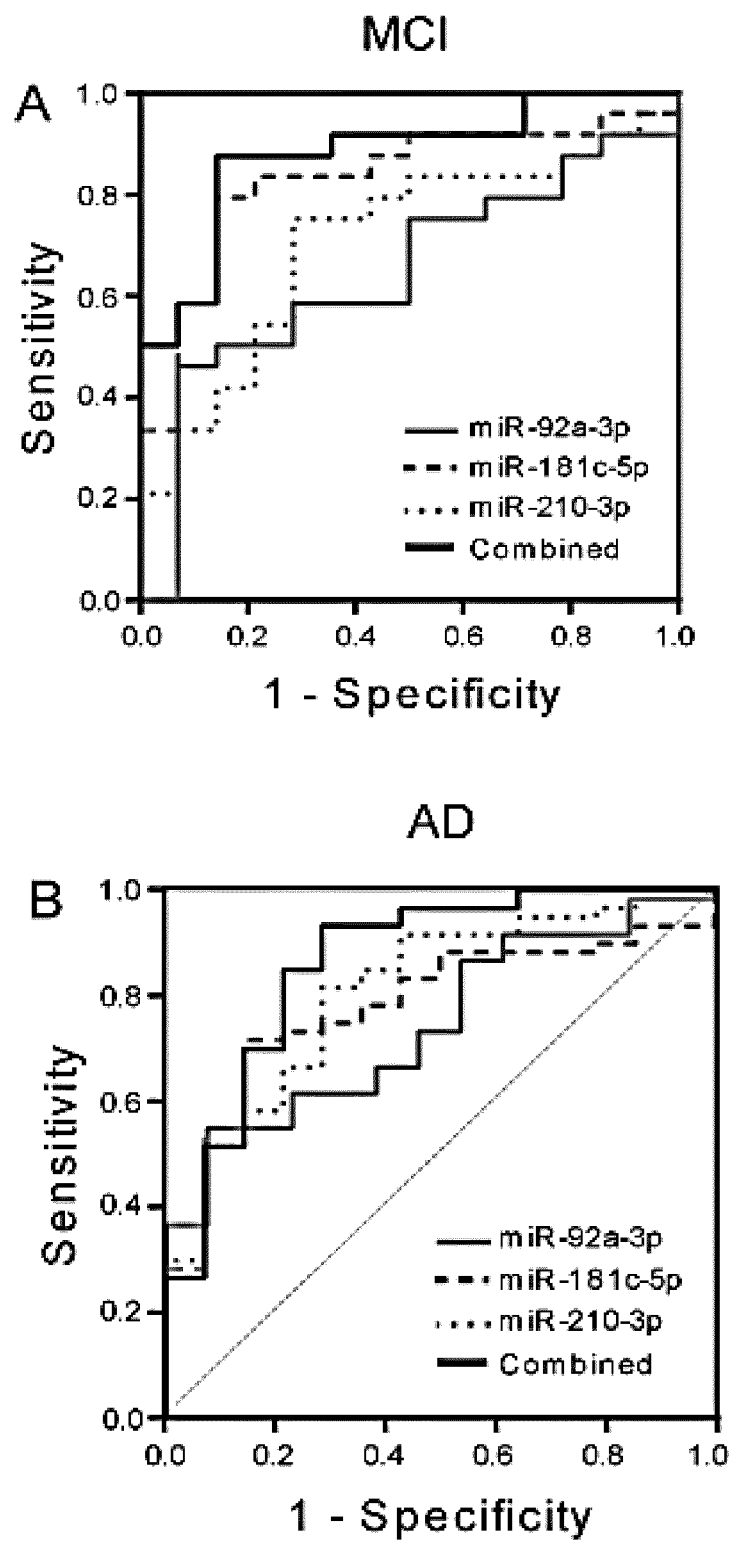
FIG. 2. miRNAs were combined to reach the best predictive value. ROC curve analysis for MCI (A) and AD (B) cases are shown. Values for males (C-D) and females (E-F) are represented separately.
Figure 2:
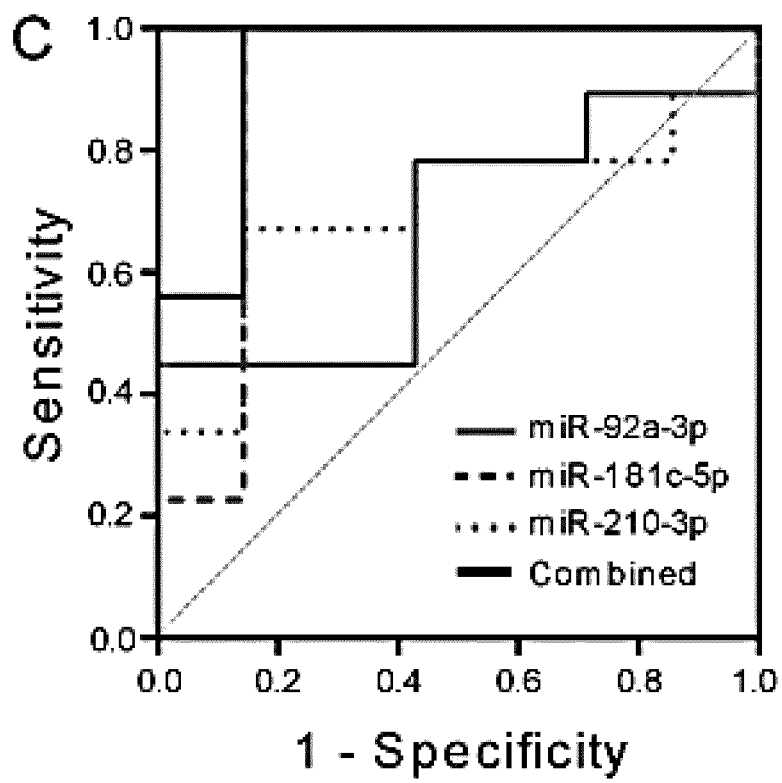
Figure 2:
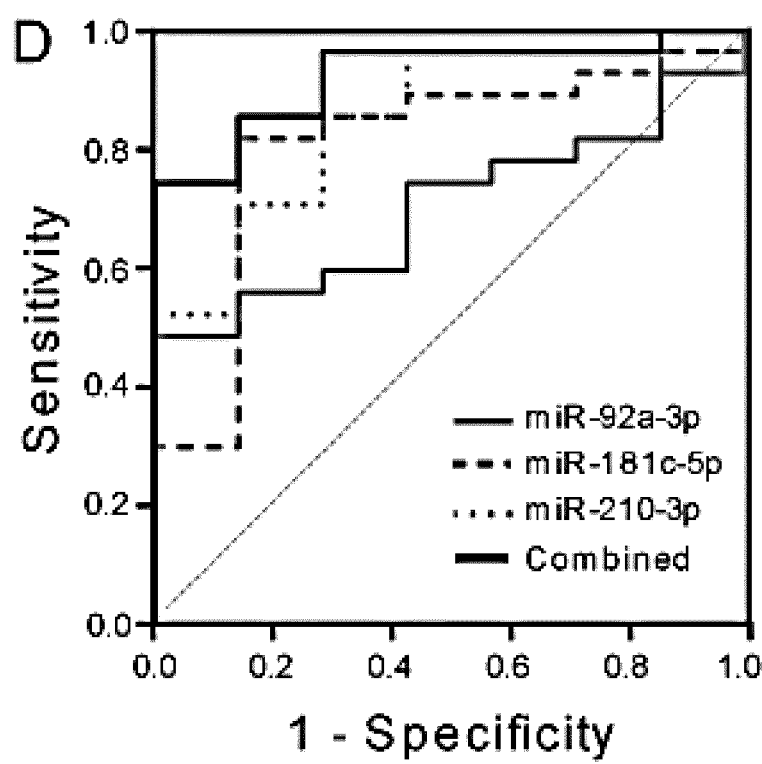
Figure 2:
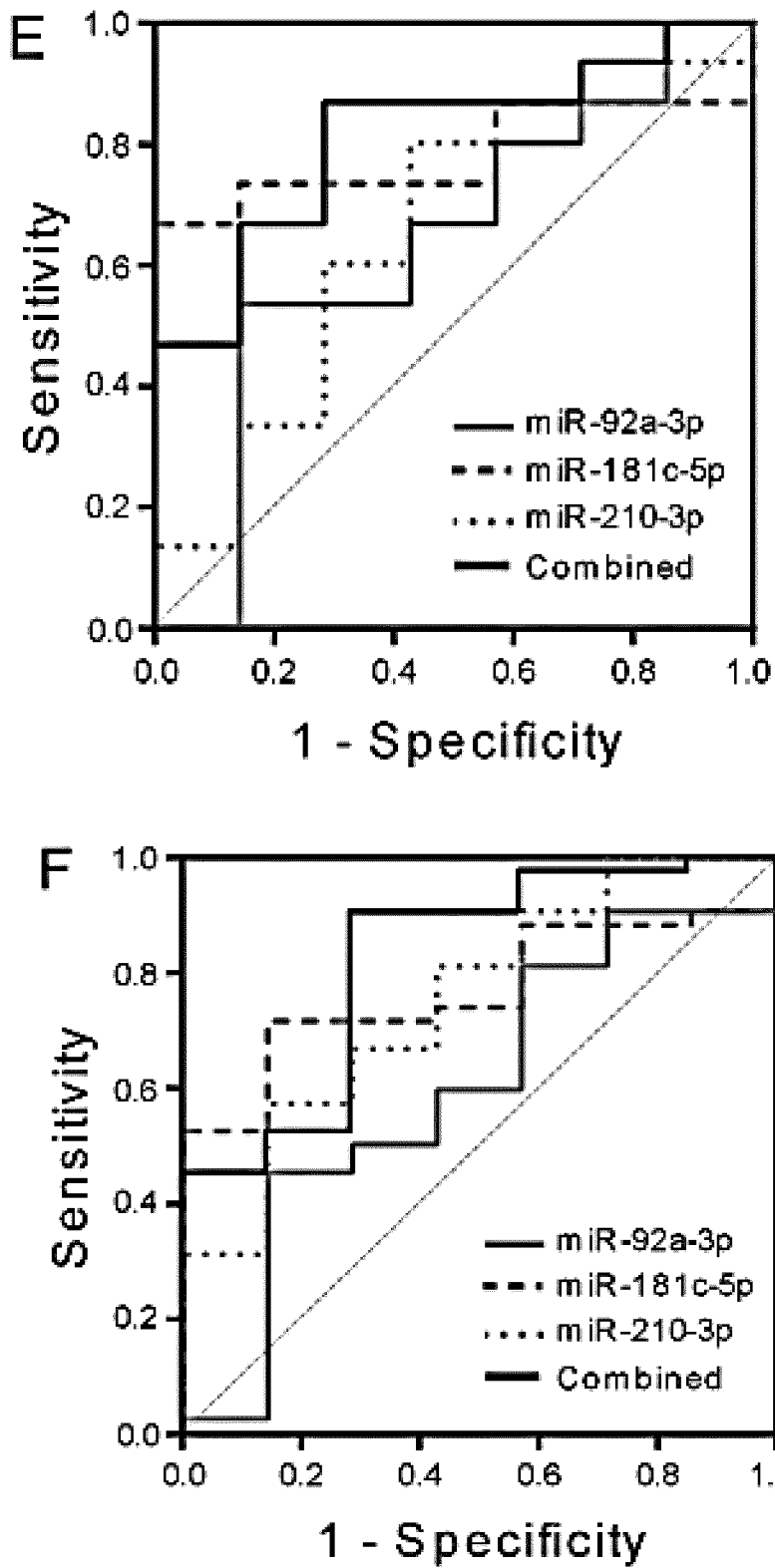

Consequently, this analysis demonstrated that the panel of three miRNAs biomarkers of the invention clearly separate MCI and AD samples from control samples, specifically plasma samples, with specificity, sensitivity and accuracy (area under the ROC, AUC) values given for each miRNA in Tables 3 and 4 and also in FIG. 1 and FIG. 2.

The next step was to look for eventual sex-dependent differences in the diagnostic potential of the panel of the miRNAs biomarkers of the present invention (FIG. 2C to 2F). The data show that a slightly better diagnostic values for male when distinguishing MCI from healthy controls subjects (Table 3):
  a) the AUC values for female and males are 0.81 and 0.94;
  b) 86.67% and 100% sensitivity for female and male; and
  c) 71.43% and 85.71% specificity for female and male, respectively.

On the other hand, the values obtained when comparing AD with healthy control subjects indicated a better diagnostic specificity and a lower sensitivity for male than female (Table 4):
  a) the AUC values for female and males are 0.82 and 0.92;
  b) 90.48% and 74.07% sensitivity for female and male;
  c) 71.43% and 100% specificity for females and males, respectively.

Figure 3:
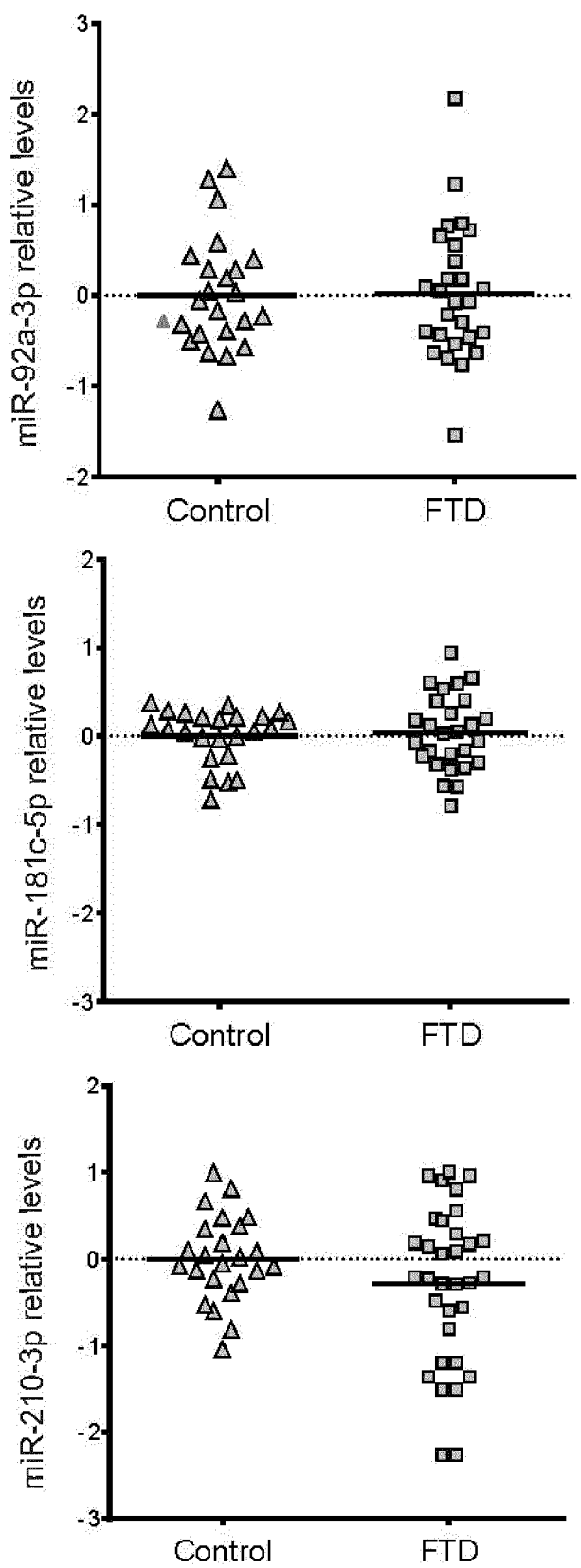
FIG. 3. Plasma miRNA levels in FTD compared to cognitively normal controls. Log2 transformed data were normalized versus the geometric mean of miR-191-5p and miR-484 levels.

Example 2. Expression Levels of the Panel of the Biomarkers of the Present Invention, miR92a, miR181c and miR210, are not Affected in FTD Patients In order to determine if the changes observed miR-92a-3p (SEQ ID NO: 1), miR-181c-5p (SEQ ID NO: 2) and miR-210-3p (SEQ ID NO: 3) were specific of MCI and AD subjects, it was decided to analyse plasma samples from a cohort of FTD patients. The results (FIG. 3) point out that the expression levels of none of the above mentioned miRNAs are changed in FTD confirming that the upregulation observed in MCI and AD patients are not observed in other dementia related subjects.

Consequently, the data show in the present disclosure, demonstrate that the panel of miRNAs biomarker selected from miR-92a-3p (SEQ ID NO: 1), miR-181c-5p (SEQ ID NO: 2) and miR-210-3p (SEQ ID NO: 3) are upregulated in a plasma sample from MCI and AD subjects versus healthy control. However, no changes were observed in the panel of biomarkers of the present invention in plasma samples from other dementia related subject, such as FTD patients. Moreover, the panel of the three miRNAs biomarkers of the present invention presented good diagnosis accuracy for distinguishing both MCI and AD subjects from healthy controls and it could be used as a reliable early diagnostic tool for distinguishing MCI and/or AD, since additionally, the panel of the invention show a high sensitivity and specificity for diagnosis of MCI and/or early stages of AD.

Figure 4:
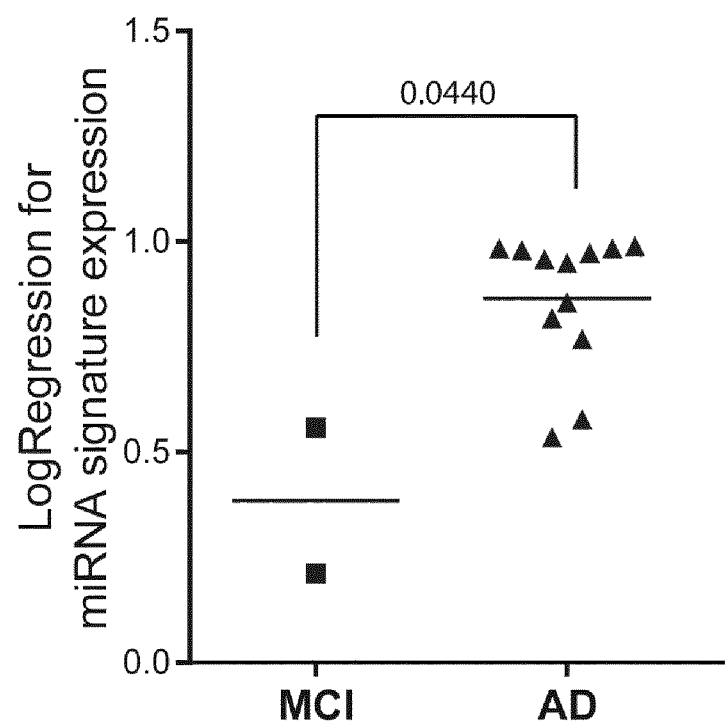
FIG. 4. Levels of miRNA signature, miR-92a-3p (SEQ ID NO: 1), miR-181c-5p (SEQ ID NO: 2) and miR-210-3p (SEQ ID NO: 3) in MCI who progressed to AD.

Example 3. Follow-Up of MCI Patients. Patients with Higher Expression Levels of the Panel of the Biomarkers of the Present Invention have More Chances to Derive to AD In order to provide further support to the value of the molecular miRNA signature as a molecular biomarker for early AD diagnosis 19 of the 26 MCI subjects for 1 to 12 years (Table) were followed-up. Three subjects diagnosed as MCI (11.5%; P4, P8 and P22) showed no cognitive impairment after 1 (P4 and P22) or 4 (P8) years and another two (P14 and P18) were still diagnosed as MCI after 3 and 11 years. The rest of cases, all developed dementia being AD the most prominent. Only one patient progressed to FTD (P7) and another to vascular dementia (P11). Interestingly, we have observed that all the MCI patients that progressed to AD have higher values of the miRNA signature compared to the MCI patients that did not evolve to AD (FIG. 4).

MCI patients were separated according to follow-up diagnosis.

From 26 patients diagnosed as MCI in the first place, 2 remained stable and 12 have progressed to AD (FIG. 5). miRNA expression levels were combined using log regression approach. Mean of miRNA signature values for each group is shown. Statistical significance was evaluated by the Mann-Whitney U test. P values of <0.05 were considered statistically significant.

The invention claimed is:

1. An in vitro method of diagnosis of Mild Cognitive Impairment (MCI) and/or early stages of Alzheimer's disease (AD) in an isolated biological sample of a subject, wherein the method comprises:
   a) quantifying the expression level of a panel of miRNAs comprising the miR-92a-3p (SEQ ID NO: 1), miR-181c-5p (SEQ ID NO: 2) and miR-210-3p (SEQ ID NO: 3) in the isolated biological sample of the subject,
   b) comparing the value obtained in step (a) to a standard value, and
   c) assigning the subject to the group of patients suffering from MCI and/or early stages of AD when the value obtained in step (a) is significantly higher than the standard value.

2. The in vitro method according to claim 1, wherein the isolated biological sample is selected from the group consisting of blood sample, serum sample, and plasma sample.

3. The in vitro method according to claim 1, wherein the isolated biological sample is plasma sample.

4. The in vitro method according to claim 1, wherein step (a) is carried out by PCR, quantitative PCR (qPCR), RT-qPCT droplet digital PCR or Southern blot.

5. The in vitro method according to claim 1, wherein step (a) is carried out by RT-qPCR.

6. The in vitro method according to claim 1, wherein the subject is a human.

7. The method of claim 1, wherein the panel of miRNAs consisting of the miR-92a-3p (SEQ ID NO: 1), miR-181c-5p (SEQ ID NO: 2) and miR-210-3p (SEQ ID NO: 3).

8. The method of claim 1, wherein quantifying the expression level of the panel of miRNAs comprises contacting the primers or probes specific for the detection and/or quantification of miR-92a-3p (SEQ ID NO: 1), miR-181c-5p (SEQ ID NO: 2) and miR-210-3p (SEQ ID NO: 3), to the isolated biological sample comprising the panel of miRNAs comprising the miR-92a-3p (SEQ ID NO: 1), miR-181c-5p (SEQ ID NO: 2) and miR-210-3p (SEQ ID NO: 3).

* * * * *

```
                             SEQUENCE LISTING

<160> NUMBER OF SEQ ID NOS: 10

<210> SEQ ID NO 1
<211> LENGTH: 22
<212> TYPE: RNA
<213> ORGANISM: Homo sapiens

<400> SEQUENCE: 1
uauugcacuu gucccggccu gu                                                 22

<210> SEQ ID NO 2
<211> LENGTH: 22
<212> TYPE: RNA
<213> ORGANISM: Homo sapiens

<400> SEQUENCE: 2
aacauucaac cugucgguga gu                                                 22

<210> SEQ ID NO 3
<211> LENGTH: 22
<212> TYPE: RNA
<213> ORGANISM: Homo sapiens

<400> SEQUENCE: 3
cugugcgugu gacagcggcu ga                                                 22

<210> SEQ ID NO 4
<211> LENGTH: 22
<212> TYPE: RNA
<213> ORGANISM: Homo sapiens

<400> SEQUENCE: 4
uuaugguuug ccugggacug ag                                                 22

<210> SEQ ID NO 5
<211> LENGTH: 22
<212> TYPE: RNA
<213> ORGANISM: Homo sapiens

<400> SEQUENCE: 5
ucaggcucag uccccucccg au                                                 22

<210> SEQ ID NO 6
<211> LENGTH: 23
<212> TYPE: RNA
<213> ORGANISM: Homo sapiens

<400> SEQUENCE: 6
caacggaauc ccaaaagcag cug                                                23

<210> SEQ ID NO 7
<211> LENGTH: 23
<212> TYPE: RNA
<213> ORGANISM: Homo sapiens

<400> SEQUENCE: 7
agguugggau cgguugcaau gcu                                                23
```

-continued

```
<210> SEQ ID NO 8
<211> LENGTH: 22
<212> TYPE: RNA
<213> ORGANISM: Homo sapiens

<400> SEQUENCE: 8
aaccaucgac cguugagugg ac                                             22

<210> SEQ ID NO 9
<211> LENGTH: 22
<212> TYPE: RNA
<213> ORGANISM: Homo sapiens

<400> SEQUENCE: 9
agccccugcc caccgcacac ug                                             22

<210> SEQ ID NO 10
<211> LENGTH: 22
<212> TYPE: RNA
<213> ORGANISM: Homo sapiens

<400> SEQUENCE: 10
gcugcgcuug gauuucgucc cc                                             22
```